United States Patent [19]

Wehner et al.

[11] Patent Number: 4,486,424
[45] Date of Patent: Dec. 4, 1984

[54] TRIORGANOTIN HYDANTOIN COMPOUNDS, AND THE USE THEREOF FOR COMBATING INSECTS AND ACARIDS

[75] Inventors: Wolfgang Wehner, Zwingenberg, Fed. Rep. of Germany; Peter Ackermann, Pfeffingen, Switzerland

[73] Assignee: Ciga-Geigy Corporation, Ardsley, N.Y.

[21] Appl. No.: 432,479

[22] Filed: Oct. 4, 1982

[30] Foreign Application Priority Data

Oct. 13, 1981 [CH] Switzerland ............ 6543/81
Aug. 11, 1982 [CH] Switzerland ............ 4808/82

[51] Int. Cl.³ ............ A01N 55/04; C07F 7/22
[52] U.S. Cl. ............ 424/245; 548/101
[58] Field of Search ............ 548/101; 424/245

[56] References Cited

U.S. PATENT DOCUMENTS

| | | | |
|---|---|---|---|
| 2,392,505 | 1/1946 | Rogers | 548/101 |
| 3,097,999 | 7/1963 | Koopmans | 424/245 X |
| 3,546,240 | 12/1970 | Bublitz | 424/245 X |
| 4,061,491 | 12/1977 | Arndt et al. | 71/92 |
| 4,110,232 | 8/1978 | Edwards | 424/245 X |

FOREIGN PATENT DOCUMENTS

| | | | |
|---|---|---|---|
| 0054516 | 6/1982 | European Pat. Off. | 424/245 |
| 0681821 | 3/1980 | U.S.S.R. | 424/245 |

*Primary Examiner*—Donald G. Daus
*Assistant Examiner*—Diana G. Rivers
*Attorney, Agent, or Firm*—Frederick H. Rabin; Bruce M. Collins

[57] ABSTRACT

Triorganotin hydantoin compounds of the formula

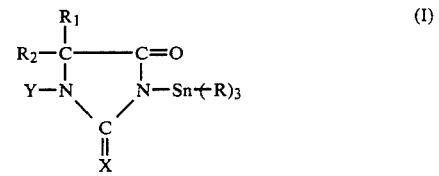

wherein
R is $C_1$–$C_8$-alkyl, $C_5$–$C_8$-cycloalkyl, phenyl or

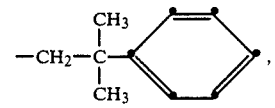

$R_1$ and $R_2$ are each hydrogen, $C_1$–$C_8$-alkyl, phenyl, hydroxyphenyl, or together they are $C_5$–$C_7$-alkylene or oxygen,
X is oxygen or sulfur, and
Y is hydrogen or —Sn—$(R)_3$, as well as a process for producing these compounds, and the use thereof for combating pests are described.

9 Claims, No Drawings

TRIORGANOTIN HYDANTOIN COMPOUNDS, AND THE USE THEREOF FOR COMBATING INSECTS AND ACARIDS

The present invention relates to triorganotin hydantoin compounds, to processes for producing them, and to the use thereof for combating pests.

The triorganotin hydantoin compounds have the formula $$\begin{array}{c} R_1 \\ | \\ R_2-C-\!\!\!-\!\!\!-C=O \\ | \quad\quad | \\ Y-N \quad N-Sn(\!\!-\!\!R)_3 \\ \;\;\;\backslash\;\;/ \\ \;\;\;\;C \\ \;\;\;\;\| \\ \;\;\;\;X \end{array} \qquad (I)$$

wherein

R is $C_1$–$C_8$-alkyl, $C_5$–$C_8$-cycloalkyl, phenyl or $$-CH_2-\underset{\underset{CH_3}{|}}{\overset{\overset{CH_3}{|}}{C}}-\!\!\!\!\bigcirc,$$

$R_1$ and $R_2$ are each hydrogen, $C_1$–$C_8$-alkyl, phenyl, hydroxyphenyl, or together they are $C_5$–$C_7$-alkylene or oxygen, X is oxygen or sulfur, and Y is hydrogen or —Sn(—R)$_3$.

The $C_1$–$C_8$-alkyl groups can be straight-chain or branched-chain. Examples of such groups are, inter alia: methyl, ethyl, propyl, isopropyl, n-, i-, sec- or tert-butyl, n-pentyl, n-hexyl, n-heptyl or n-octyl, and isomers thereof, for example 2-ethylhexyl.

The $C_5$–$C_8$-cycloalkyl groups are, inter alia: cyclopentyl, cyclohexyl or cyclooctyl, especially cyclohexyl.

Preferred compounds of the formula I are those wherein

R is $C_1$–$C_4$-alkyl, $C_5$–$C_6$-cycloalkyl, phenyl or $$-CH_2-\underset{\underset{CH_3}{|}}{\overset{\overset{CH_3}{|}}{C}}-\!\!\!\!\bigcirc,$$

$R_1$ and $R_2$ are each methyl or phenyl, or together oxygen,

X is oxygen or sulfur, and

Y is hydrogen or –(Sn—R)$_3$.

Particularly preferred compounds of the formula I are those wherein

R is n-butyl, cyclohexyl, phenyl or $$-CH_2-\underset{\underset{CH_3}{|}}{\overset{\overset{CH_3}{|}}{C}}-\!\!\!\!\bigcirc,$$

$R_1$ and $R_2$ are each methyl or phenyl, or together oxygen,

X is oxygen or sulfur, and

Y is hydrogen or –(Sn—R)$_3$.

More particularly preferred compounds of the formula I are those wherein

R is n-butyl, cyclohexyl, phenyl or $$-CH_2-\underset{\underset{CH_3}{|}}{\overset{\overset{CH_3}{|}}{C}}-\!\!\!\!\bigcirc,$$

$R_1$ and $R_2$ are each methyl or phenyl,

X is oxygen or sulfur, and

Y is hydrogen or —Sn(—R)$_3$.

The compounds of the formula I can be produced, using methods known per se, for example as follows:

$$\begin{array}{c} R_1 \\ | \\ R_2-C-\!\!\!-\!\!\!-C=O \\ | \quad\quad | \\ HN \quad NH \\ \;\;\;\backslash\;\;/ \\ \;\;\;\;C \\ \;\;\;\;\| \\ \;\;\;\;X \end{array} + (R)_3Sn-OH \text{ or } (R)_3SnOSn(-R)_3 \longrightarrow I.$$

(II) \qquad (III) \qquad (IV)

In the formulae II, III and IV, the symbols R, $R_1$, $R_2$ and X have the meanings defined under the formula I.

The process is advantageously performed at a temperature of between 30° and 180° C., preferably between 80° and 150° C., under normal or slightly reduced pressure, and preferably in the presence of a solvent or diluent inert to the reactants. Suitable solvents or diluents are, for example: halogenated or non-halogenated hydrocarbons, such as petroleum ether, toluene, chloroform or methylene chloride; alcohols, such as methanol and ethanol or isopropanol; ethers and ethereal compounds, such as diethyl ether, dioxane and tetrahydrofuran; ketones, such as acetone, cyclohexanone or methyl ethyl ketone. The starting materials of the formulae II, III and IV are known, and they can be produced by known methods.

The compounds of the formula I are suitable for combating various pests on animals and plants. They also have an action regulating plant growth. The compounds of the formula I are suitable for combating in particular all development stages of phytopathogenic and zooparasitic insects, for example of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, and also phytopathogenic and zooparasitic mites and ticks of the order Acarina.

Compounds of the formula I are especially suitable for combating eating insects, for example Anthonomus grandis, and for combating mites which damage plants, for example Tetranychus urticae and Tetranychus cinnabarinus.

Active substances of the formula I also have a very favourable action against flies, for example Musca domestica, and against mosquito larvae. The compounds of the formula I are also distinguished by a broad ovicidal and ovilarvicidal action. Active substances of the formula I also have a very good fungicidal action. Compounds of the formula I are thus effective against the phytopathogenic fungi belonging to the following classes: Ascomycetes (for example Erysiphaceae, Fusarium and Helminthosporium); Basidiomycetes, such as Puccinia, Rhizoctonia, Tilletia and Hemileia; Fungi imperfecti (for example Cercospora, Botrytis and Septoria); Phycomycetes, such as Phytophthora. Furthermore, the compounds of the formula I have a systemic action. The compounds of the formula I are advantageously used as dressing agents for the treatment of seed and provisions (fruits, tubers, grain, and so forth) and plant cuttings to protect them from fungus infections, and also against phytopathogenic fungi occurring in the soil.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objects to be achieved and the given conditions.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$-$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publication: "Mc Cutcheon's Detergents and Emulsifiers Annual", MC Publishing Corp., Ringwood, N.J., 1979.

The pesticidal preparations contain as a rule 0.1 to 99%, particularly 0.1 to 95%, of active substance of the formula I, 1 to 99.9% of a solid or liquid additive, and 0 to 25%, especially 0.1% to 25%, of a tenside. Whereas commercial products are preferably in the form of concentrated compositions, the compositions employed by the end-user are as a rule diluted.

The compositions can also contain additives such as stabilisers, antifoam agents, viscosity regulators, binders and adhesives, as well as fertilisers or other active substances for obtaining special effects.

Formulation examples for liquid active substances of the formula I (%=percent by weight)

| 1. Emulsion concentrates | (a) | (b) | (c) |
|---|---|---|---|
| active substance, | 20% | 40% | 50% |
| calcium dodecylbenzenesulfonate | 5% | 8% | 5.8% |
| castor oil-polyethylene glycol ether (36 mols of ethylene oxide) | 5% | — | — |
| tributylphenol-polyethylene glycol ether (30 mols of ethylene oxide) | — | 12% | 4.2% |
| cyclohexanone | — | 15% | 20% |
| xylene mixture | 70% | 25% | 20% |

Emulsions of any required concentration can be produced from concentrates of this type by dilution with water.

| 2. Solutions | (a) | (b) | (c) | (d) |
|---|---|---|---|---|
| active substance | 80% | 10% | 5% | 95% |
| ethylene glycol-monomethyl ether | 20% | — | — | — |
| polyethylene glycol M G 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of the smallest possible drops.

| 3. Granulates | (a) | (b) |
|---|---|---|
| active substance | 5% | 10% |
| kaolin | 94% | — |
| highly dispersed silicic acid | 1% | — |
| attapulgite | — | 90% |

The active substance is dissolved in methylene chloride, the solution is sprayed onto the carrier, and the solvent is subsequently evaporated off in vacuo.

| 4. Dusts | (a) | (b) |
|---|---|---|
| active substance | 2% | 5% |
| highly dispersed silicic acid | 1% | 5% |
| talcum | 97% | — |
| kaolin | — | 90% |

Ready-for-use dusts are obtained by the intimate mixing together of the carriers with the active substance.

Formulation examples for solid active substances of the formula I (%=percent by weight)

| 5. Wettable powders | (a) | (b) |
|---|---|---|
| active substance | 20% | 60% |
| sodium lignin sulfonate | 5% | 5% |
| sodium lauryl sulfate | 3% | — |
| sodium diisobutylnaphthalene sulfonate | — | 6% |
| octylphenolpolyethylene glycol ether (7–8 mols of ethylene oxide) | — | 2% |
| highly dispersed silicic acid | 5% | 27% |
| kaolin | 67% | — |

The active substance is well mixed with the additives and the mixture is thoroughly ground is a suitable mill. Wettable powders which can be diluted with water to give suspensions of the required concentration are obtained.

| 6. Emulsion concentrate | |
|---|---|
| active substance | 10% |
| octylphenol polyethylene glycol ether (4–5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| 7. Dusts | (a) | (b) |
|---|---|---|
| active substance | 5% | 8% |
| talcum | 95% | — |
| kaolin | — | 92% |

Dusts ready for use are obtained by mixing the active substance with the carrier and grinding the mixture in a suitable mill.

| 8. Extruder granulate | |
|---|---|
| active substance | 10% |
| sodium lignin sulfonate | 2% |
| carboxymethylcellulose | 1% |
| kaolin | 87% |

The active substance is mixed and ground with the additives, and the mixture is moistened with water. This mixture is extruded and then dried in a stream of air.

| 9. Coated granulate | |
|---|---|
| active substance | 3% |
| polyethylene glycol (M G 200) | 3% |
| kaolin | 94% |

The finely ground active substance is evenly applied, in a mixer, to the kaolin moistened with polyethylene glycol. Dustfree coated granulates are obtained in this manner.

| 10. Suspension concentrate | |
|---|---|
| active substance | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active substance is intimately mixed with the additives. There is thus obtained a suspension concentrate from which can be produced, by dilution with water, suspensions of the concentration required.

EXAMPLE 1

Production of 1,3-bis-triphenyltin-5,5-dimethylhydantoin

A suspension of 64.1 g of 5,5-dimethylhydantoin and 367.0 g of triphenyltin hydroxide in 400 ml of toluene is refluxed for 5 hours, the reaction water formed being azeotropically distilled off during the process. After cooling, the solution is filtered until clear, and is subsequently freed in vacuo from volatile constituents.

There is thus obtained the compound of the formula 5

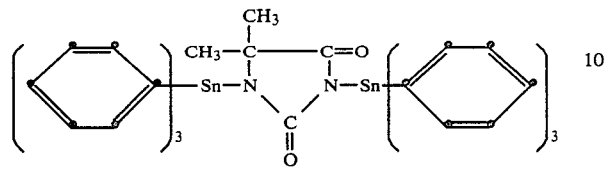

in crystalline form having a melting point of 138°–140° C. The following compounds are produced in an analogous manner:

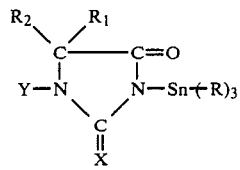

| R | $R_1$ | $R_2$ | X | Y | Physical data |
|---|---|---|---|---|---|
| ⌬–H | $CH_3$ | $CH_3$ | O | $-Sn(-R)_3$ | m.p.: 245–248° C. |
| $-C_4H_{9(n)}$ | H | H | S | $-Sn(-R)_3$ | viscous oil |
| $-C_4H_{9(n)}$ | H | H | O | $-Sn(-R)_3$ | viscous oil |
| $-C_4H_{9(n)}$ | $CH_3$ | $CH_3$ | O | H | m.p.: 50–51° C. |
| ⌬–H | $CH_3$ | $CH_3$ | O | H | m.p. 222–224° C. |
| $-C_4H_{9(n)}$ | ⌬ | ⌬ | O | H | m.p. 38–39° C. |
| ⌬–H | ⌬ | ⌬ | O | H | m.p. 198–200° C. |
| $-C_4H_{9(n)}$ | ⌬ | ⌬ | O | $-Sn(-R)_3$ | viscous oil |
| $-C_4H_{9(n)}$ | ⌬ | ⌬ | S | H | m.p. 58–60° C. |
| $-C_4H_{9(n)}$ | ⌬ | ⌬ | S | $-Sn(-R)_3$ | viscous oil |
| $-C_4H_{9(n)}$ | $CH_3$ | $CH_3$ | O | $-Sn(-R)_3$ | viscous oil |
| $-C_4H_{9(n)}$ | $-(CH_2)_5-$ | | O | H | m.p.: 80–82° C. |
| $C_4H_{9(n)}$ | $-O-$ | | O | $-Sn(-R)_3$ | viscous oil |
| ⌬–H | $-O-$ | | O | $-Sn(-R)_3$ | m.p.: 217–219° C. |
| ⌬ | $-O-$ | | O | H | m.p.: 180–182° C. |

-continued

| R | R₁ | R₂ | X | Y | Physical data |
|---|---|---|---|---|---|
| 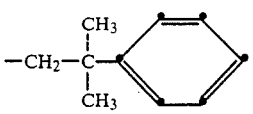 | —O— | | O | —Sn(R)₃ | m.p.: 115–116° C. |
| 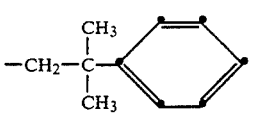 | CH₃ | CH₃ | O | H | |
| 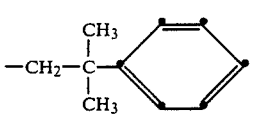 | CH₃ | CH₃ | O | —Sn(R)₃ | |
| 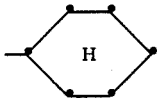 | 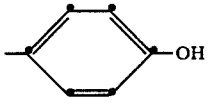 | | H | O | —Sn(R)₃ |
| 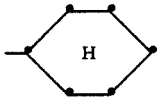 | 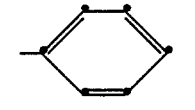 | 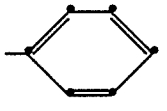 | | O | —Sn(R)₃ |
| 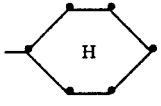 | 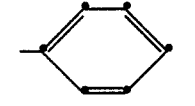 |  | | S | H |
| 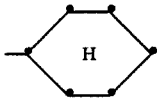 |  | 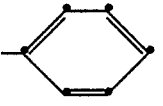 | | S | —Sn(R)₃ |

EXAMPLE 2

Insecticidal action against *Anthonomus grandis*

Cotton plants in the 4- to 5-leaf stage are sprayed dripping wet with a test solution containing, per 100 liters of water, 25 g and 50 g, respectively, of the active substance to be tested. After the drying of the applied coating, 5 *Anthonomus grandis* beetles are settled onto each plant. Two plants are used per active substance and per concentration. An evaluation of the mortality rate obtained is made after 24, 48 and 120 hours. The tests are carried out at 24° C. with 60% relative humidity. Compounds according to the Production Example exhibit activity against *Anthonomus grandis*.

EXAMPLE 3

Action against plant-damaging acarides: *Tetranychus urticae* (OP-sensitive) and *Tetranychus cinnabarinus* (OP-tolerant)

The primary leaves of *Phaseolus vulgaris* plants are infested, 16 hours before the test for acaricidal action, with an infested piece of leaf from a mass culture of *Tetranychus urticae* (OP-sensitive) and *Tetranychus cinnabarinus* (OP-tolerant), respectively (tolerance is with respect to compatibility with Diazinon). The infested plants treated in this manner are sprayed dripping wet with test solutions containing 400 and 200 ppm, respectively, of the compound to be tested. An assessment is made after 24 hours and again after 7 days, by examination of the imagines and larvae (all mobile stages) under a binocular microscope, of the living and of the dead individuals. One plant is used per concentration and per test series. The plants are standing during the test in greenhouse compartments at 25° C.

Within the concentration limits given above, compounds according to the Production Example have a 100% action against individuals of the species *Tetranychus urticae* and *Tetranychus cinnabarinus*.

EXAMPLE 4

Action against *Botrytis cinerea* on braod beans

Broad-bean plants about 10 cm in height are sprayed with a spray liquor produced from wettable powder of the active substance (0.02% of active substance). The treated plants are infested after 24 hours with a conidiospore suspension of the fungus. After incubation of the infested plants for 2–3 days at 21° C. with 95–100% relative humidity, an assessment is made of the extent of fungus infection. Compounds according to the Production Example have a 100% action against *Botrytis cinerea*.

EXAMPLE 5

Residual-protective action against *Venturia inaequalis* on apple shoots

Apple seedlings having 10–20 cm long fresh shoots are sprayed with a spray liquor prepared from wettable powder of the active substance (0.06% of active substance). The treated plants are sprayed after 24 hours with a conidiospore suspension of the fungus. The plants are then incubated for 5 days with 90–100% relative humidity, and for a further 10 days they are kept at 20°–24° C. in a greenhouse. The extent of scab infection is assessed 15 days after infestation. Compounds according to the Production Example reduce infection to less than 10%. The level of Venturia infection on infested but untreated shoots is 100%.

EXAMPLE 6

Action against *Cercospora arachidicola* on groundnut plants (a) Residual-protective action Groundnut plants 10–15 cm in height are sprayed with a spray liquor produced from wettable powder of the active substance (0.006% of active substance); and 48 hours later they are infested with a conidiospore suspension of the fungus. The infested plants are incubated for 72 hours at about 21° C. with high relative humidity, and are subsequently kept in a greenhouse until the typical leaf spots have appeared. The assessment of the fungicidal action is made 12 days after infestation, and is based on the number and size of the occurring spots.

(b) Systemic action

A spray liquor prepared from wettable powder of the active substance (0.06% of active substance, relative to the volume of soil) is applied to the soil of groundnut plants 10–15 cm in height. After 48 hours, the treated plants are infested with a conidiospore suspension of the fungus, and are then incubated for 72 hours at about 21° C. with high relative humidity. The plants are subsequently transferred to a greenhouse and an assessment of fungus infection is made after 11 days.

Compared with infested but untreated control plants (number and size of spots=100%), groundnut plants which have been infested but treated with active substances according to the Production Example exhibit a greatly reduced amount of Cercospora infection.

What is claimed is:

1. A compound of the formula:

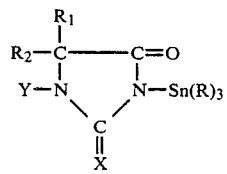

wherein
R is alkyl of 1 to 8 carbon atoms, cycloalkyl of 5 to 8 carbon atoms, phenyl or 2-methyl-2-phenylpropyl;
each of $R_1$ and $R_2$, when taken independently of the other is hydrogen, alkyl of 1 to 8 carbon atoms, phenyl, or hydroxyphenyl, or
$R_1$ and $R_2$ taken together are oxygen or alkylene of 5 to 7 carbon atoms;
X is oxygen or sulfur; and
Y is hydrogen or $Sn(R)_3$ in which R is as defined above.

2. A compound according to claim 1 wherein
R is alkyl of 1 to 4 carbon atoms; cyclopentyl; cyclohexyl, phenyl or 2-methyl-2-phenylpropyl; and
each of $R_1$ and $R_2$ when taken independently of the other, is methyl or phenyl; or
$R_1$ and $R_2$ taken together are oxygen.

3. A compound according to claim 2 wherein R is n-butyl, cyclohexyl, phenyl or 2-methyl-2-phenylpropyl.

4. A compound according to claim 3 wherein each of $R_1$ and $R_2$ is methyl or phenyl.

5. The compound according to claim 1 which has the formula

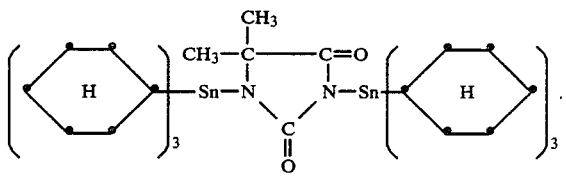

6. The compound according to claim 1 which has the formula

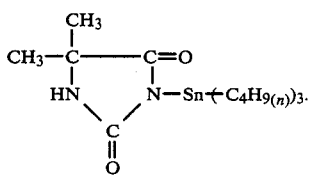

7. The compound according to claim 1 which has the formula

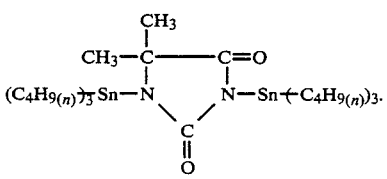

8. A composition for combatting insects and acarids which comprises an effective amount of a compound according to claim 1 in combination with a carrier.

9. The method of combatting insects and acarids which comprises applying thereto or to their locus an effective amount of a compound according to claim 1.

* * * * *